US009116079B2

(12) United States Patent
Gunter (10) Patent No.: US 9,116,079 B2
(45) Date of Patent: Aug. 25, 2015

(54) DYNAMIC TEST FIXTURE

(71) Applicant: ABT, INC., Troutman, NC (US)

(72) Inventor: Charles E. Gunter, Mooresville, NC (US)

(73) Assignee: ABT, INC., Troutman, NC (US)

(*) Notice: Subject to any disclaimer, the term of this patent is extended or adjusted under 35 U.S.C. 154(b) by 215 days.

(21) Appl. No.: 13/940,951

(22) Filed: Jul. 12, 2013

(65) Prior Publication Data

US 2014/0013856 A1    Jan. 16, 2014

Related U.S. Application Data

(60) Provisional application No. 61/671,177, filed on Jul. 13, 2012.

(51) Int. Cl.
```
G01N 3/08    (2006.01)
G01M 5/00    (2006.01)
G01N 3/10    (2006.01)
```

(52) U.S. Cl.
CPC .............. *G01N 3/08* (2013.01); *G01M 5/0075* (2013.01); *G01N 3/10* (2013.01); *G01N 2203/0016* (2013.01); *G01N 2203/0019* (2013.01); *G01N 2203/0252* (2013.01)

(58) Field of Classification Search
CPC ... G01N 3/08; G01N 3/10; G01N 2203/0252; G01N 2203/0016; G01N 2203/0019
USPC .................... 73/818, 819, 821, 825
See application file for complete search history.

(56) References Cited

U.S. PATENT DOCUMENTS 3,592,041 A * 7/1971 Spencer ............................ 73/7
6,393,890 B1   5/2002 Scholeck

FOREIGN PATENT DOCUMENTS

JP      2003-194688 A    7/2003
KR   10-2002-0050599 A   6/2002
(Continued)

OTHER PUBLICATIONS

The International Bureau of WIPO. PCT International Preliminary Report on Patentability dated Jan. 13, 2015. International Application No. PCT/US2013/050299. International Filing Date: Jul. 12, 2013. Name of Applicant: ABT, Inc. English Language. 6 pages.
(Continued)

*Primary Examiner* — Lisa Caputo
*Assistant Examiner* — Jonathan Dunlap
(74) *Attorney, Agent, or Firm* — Moore & Van Allen PLLC (57) ABSTRACT

A text fixture apparatus for testing structures with a compression testing machine. The test fixture apparatus includes a support plate assembly and a load plate assembly. The support plate assembly includes two parallel support plates and has sloped surfaces to support a first and second structures and angles of equal magnitude and opposite slope. The load plate assembly is configured to oppose the support plate assembly, includes at least one load plate, and allows the load plate assembly to apply a load to the structures in response force on the support plate assembly, load plate assembly, or a combination thereof in a direction other than perpendicular to the sloped surfaces. A vertical force applied by the assemblies results in substantially equal and opposite horizontal components of force on the first structure and the second structure. Methods of testing and of making the apparatus are provided.

26 Claims, 7 Drawing Sheets

(56) References Cited

FOREIGN PATENT DOCUMENTS

| KR | 10-2009-0079420 A | 7/2009 |
| KR | 10-1036291 B1 | 7/2010 |

OTHER PUBLICATIONS

Korean Intellectual Property Office, International Search Report and Written Opinion dated Oct. 14, 2013, pp. 1-9.

* cited by examiner

DYNAMIC TEST FIXTURE

CROSS-REFERENCE TO RELATED APPLICATION

This application claims the benefit of U.S. Patent Application No. 61/671,177, filed Jul. 13, 2012, the entire contents of which are hereby incorporated by reference.

FIELD

Embodiments disclosed herein relate generally to testing of structures, and more particularly may relate to fixtures for applying a load to structures with a compression-type machine.

BACKGROUND

Trench drains often have a grate across their top opening that must support loads that may include heavy vehicles. Grates are currently tested to certain industry standards, such as those promulgated by the American Association of State Highway and Transportation Officials (AASHTO) in AASHTO M306 "Standard Specification for Drainage, Sewer, Utility, and Related Castings." Current testing equipment includes proof load compression machines, also referred to as test presses, which may have a static upper platen and a vertically moveable, hydraulically driven lower platen. With such a machine, when a component is to be tested, the component is placed on the lower platen, the lower platen is raised until the component contacts the bottom surface of the top platen, and then the compression test is performed.

Current testing machines and apparatus, however, generally impart only a load that is perpendicular to the surface of the tested grate, which may be a vertical load. Actual dynamic loads encountered, such as when a tire impacts the grate in use, also include a horizontal component. Thus, a need exists for a test apparatus that applies a load to a grate at an angle of other than 90 degrees to simulate actual use.

SUMMARY

In accordance with one embodiment disclosed herein, a text fixture apparatus for testing first and second structures with a compression testing machine is provided. The test fixture apparatus includes a support plate assembly and a load plate assembly. The support plate assembly includes two spaced, parallel support plates in fixed relation and parallel to a first central longitudinal plane. The support plate assembly also has sloped surfaces associated with each support plate to support the first structure at a first angle relative to horizontal and the second structure at a second angle relative to horizontal, with the first angle and the second angle being of equal magnitude and opposite slope. The load plate assembly is configured to oppose the support plate assembly. The load plate assembly includes at least one load plate parallel to a second central longitudinal plane, and is configured to allow the load plate assembly to apply a load to the first structure and to the second structure in response to application of force to the support plate assembly, load plate assembly, or a combination thereof in a direction other than perpendicular to the sloped surfaces.

In some such embodiments, the test fixture apparatus further includes a first load contact plate having a first surface and a second load contact plate having a second surface. The first load contact plate and the second load contact plate are each mounted to the at least one load plate. When the load plate assembly opposes the support plate assembly with the first and second structures disposed therebetween and the first and second central longitudinal planes are parallel and in vertical alignment, the first surface of the first load contact plate is oriented at the first angle relative to horizontal and the second surface of the second load contact plate is a oriented at the second angle relative to horizontal. In some such embodiments, the first load contact plate and the second load contact plate each have a width that is transverse to the second central longitudinal plane and that is less than the distance between the support plates. In some embodiments and in combination with any of the above embodiments, the test fixture apparatus also includes at least one buffer plate adjacent to the first surface of the first load contact plate and at least one other buffer plate adjacent to the second surface of the second load contact plate.

In some embodiments and in combination with any of the above embodiments, the support plates are spaced by a distance transverse to the first central longitudinal plane that permits rails of the first structure to be received by the sloped surfaces that are at the first angle and rails of the second structure to be received by the sloped surfaces that are at the second angle. In some such embodiments, the rails of the first structure and the rails of the second structure are parallel to the support plates.

In some embodiments and in combination with any of the above embodiments, the sloped surface at the first angle and the sloped surface at the second angle associated with each support plate terminate proximate to each other with a stop disposed therebetween. In some such embodiments, the stop includes a protrusion configured to separate the first structure and the second structure.

In some embodiments and in combination with any of the above embodiments, the sloped surface at the first angle and sloped surface at the second angle associated with each support plate slope downward from each respective outer end of the support plate toward a central portion of the support plate to terminate proximate to each other.

In some embodiments and in combination with any of the above embodiments, the sloped surfaces at the first angle and sloped surfaces at the second angle on each support plate slope upward from each respective outer end of the support plate toward a central portion of the support plate to terminate proximate to each other.

In some embodiments and in combination with any of the above embodiments, when the load plate assembly opposes the support plate assembly with the first central longitudinal plane parallel and in vertical alignment with the second central longitudinal plane, and with the first structure and the second structure disposed therebetween, a vertical force applied results in substantially equal and opposite horizontal components of force on the first structure and the second structure.

In some embodiments and in combination with any of the above embodiments, the at least one load plate includes two spaced, parallel support plates in fixed relation.

In accordance with another embodiment disclosed herein, another test fixture apparatus for testing first and second structures with a compression testing machine is provided, The apparatus includes a support and a load assembly. The support has sloped surfaces configured to support the first structure at a first angle relative to horizontal and the second structure at a second angle relative to horizontal, the first angle and the second angle being of equal magnitude and opposite slope. The load assembly is configured to oppose the support, and includes at least one load member configured to allow the load assembly to apply a load to the first structure and to the second structure in response to application of force to the support, load assembly, or a combination thereof in a direction other than perpendicular to the sloped surfaces, and a first load applying portion having a first surface and a second load applying portion having a second surface.

In some such embodiments, when the load assembly opposes the support with the first and second structures disposed therebetween, the first surface of the first load applying portion is oriented at the first angle relative to horizontal and the second surface of the second load applying portion is oriented at the second angle relative to horizontal, and a force applied in a direction that substantially bisects the angle formed by the sloped surfaces results in substantially equal and opposite horizontal components of force on the first structure and the second structure. In some such embodiments, each sloped surface at the first angle terminates proximate to a corresponding sloped surface at the second angle with a stop disposed therebetween. In some such embodiments, the stop includes a protrusion configured to separate the first structure and the second structure.

In some embodiments and in combination with any of the above embodiments, the sloped surfaces are spaced by a distance that are configured to permit rails of the first structure to be received by the sloped surfaces that are at the first angle and rails of the second structure to be received by the sloped surfaces that are at the second angle, wherein the rails of the first structure and the rails of the second structure are parallel to each other.

In accordance with another embodiment disclosed herein, a method of testing first and second structures using a test fixture is provided. The method includes placing the first structure on a support that supports the structure at a first angle relative to horizontal and placing the second structure on the support, the support supporting the second structure at a second angle relative to horizontal of equal magnitude and opposite slope to the first angle. A load is applied to the first structure in a first direction and to the second structure in a second direction until reaching a failure mode of at least one structure. In some such embodiments, applying the load to the first structure in a first direction includes applying a load through a first plate having a surface parallel to the first angle and applying the load to the second structure in a second direction includes applying a load through a second plate having a surface parallel to the second angle.

In some embodiments and in combination with any of the above embodiments, the first structure and the second structure are grates each having a top and a bottom, each grate including parallel rails and cross-bars extending therebetween, and further including applying force in a second direction to the bottom of the rails with the support and applying force in an opposite third direction to the cross-bars.

In some embodiments and in combination with any of the above embodiments, placing the first structure on a support and placing the second structure on the support includes placing the first structure and the second structure on a support plate assembly including two spaced, parallel support plates in fixed relation and parallel to a first central longitudinal plane. The support plate assembly has sloped surfaces associated with each support plate to support the first structure at a first angle relative to horizontal and the second structure at a second angle relative to horizontal, the first angle and the second angle being of equal magnitude and opposite slope. Applying a load to the first structure in a first direction and to the second structure in a second direction includes applying a load to a load plate assembly that is configured to oppose the support plate assembly. The load plate assembly includes at least one load plate parallel to a second central longitudinal plane and is configured to allow the load plate assembly to apply a load to the first structure and to the second structure in response to application of force to the support plate assembly, load plate assembly, or a combination thereof in a direction other than perpendicular to the sloped surfaces.

In accordance with another embodiment disclosed herein, a method of making a test fixture for testing first and second structures is provided. The method includes assembling two support plates to be spaced, parallel, and in fixed relation, each support plate having sloped surfaces to support the first structure at a first angle relative to horizontal and the second structure at a second angle relative to horizontal, the first angle and the second angle being of equal magnitude and opposite slope. Two load plates are assembled to be spaced, parallel, and in fixed relation. A load contact plate is mounted to each load plate, with the load contact plates configured to apply a load to the first structure and to the second structure in response to application of force to the support plates, load plates, or a combination thereof in a direction other than perpendicular to the sloped surfaces. In some such embodiments, assembling the support plates includes attaching the support plates to each other with elongated threaded fasteners and nuts. In some such embodiments, assembling the load plates includes attaching the load plates to each other with elongated threaded fasteners and nuts. In some such embodiments, mounting load contact plates to the load plates includes attaching the load contact plates to the load plates with threaded fasteners. In some such embodiments, the method includes varying the spacing of the support plates and the load plates with use of varying length threaded fasteners and varying width load contact plates to accommodate varying width structures.

BRIEF DESCRIPTION OF THE DRAWINGS

For a more complete understanding, reference should now be had to the embodiments shown in the accompanying drawings and described below. In the drawings.

DESCRIPTION

The following detailed description of embodiments refers to the accompanying drawings, which illustrate specific embodiments. Other embodiments having different structures and operation do not depart from the scope of the present disclosure.

Certain terminology is used herein for convenience only and is not to be taken as a limitation on the embodiments described. For example, words such as "top", "bottom", "upper," "lower," "left," "right," "horizontal," "vertical," "upward," and "downward" merely describe the configuration shown in the figures. Indeed, the referenced components may be oriented in any direction and the terminology, therefore, should be understood as encompassing such variations unless specified otherwise. Throughout this disclosure, where a process or method is shown or described, the method may be performed in any order or simultaneously, unless it is clear from the context that the method depends on certain actions being performed first.

Figure 1:
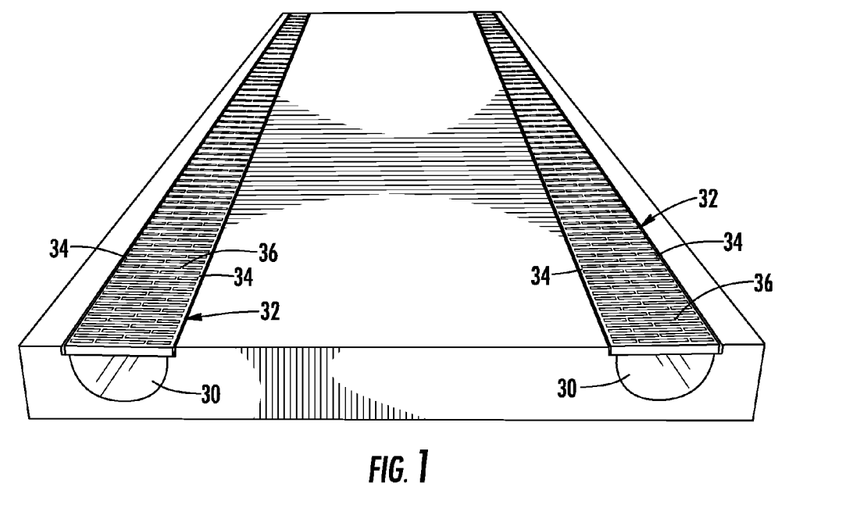
FIG. 1 shows an exemplary installation of grates on trench drains.
Figure 2:
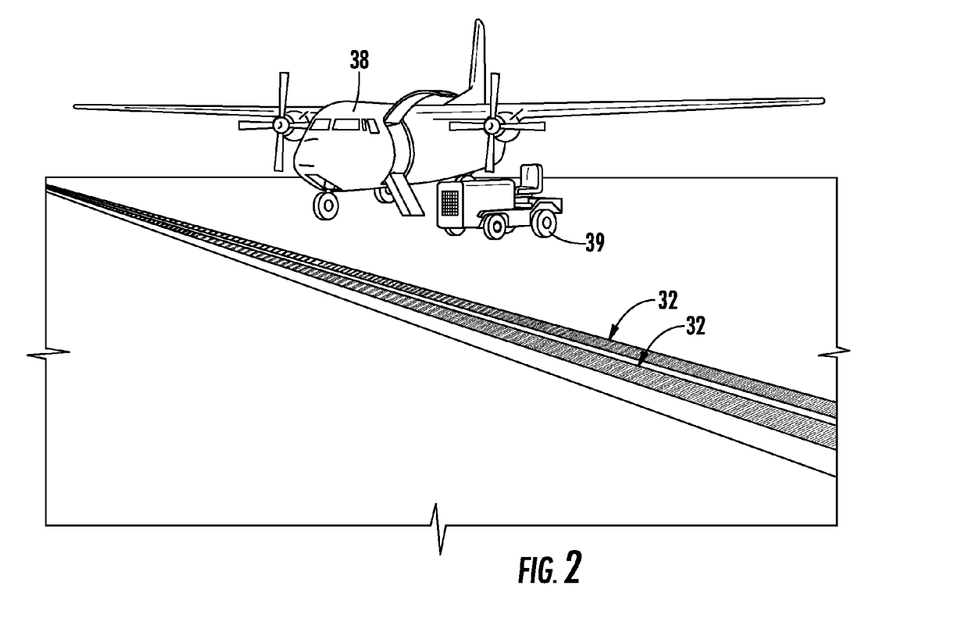
FIG. 2 shows another exemplary installation of grates on trench drains.

Referring to the drawings, where like reference numerals refer to the same or similar parts, FIG. 1 shows an example of parallel trench drains 30 with grates 32 at the top of the drains. The grates 32 have parallel rails 34 resting on support surfaces formed at the upper ends of the trench drains 30 and may have cross-bars 36 or other features between and connecting the rails 34. FIG. 2 shows another example of parallel trench drains and grates 32 at an airport, where large dynamic loads may be experienced by the grates 32 from aircraft and other heavy vehicles.

Figure 3:
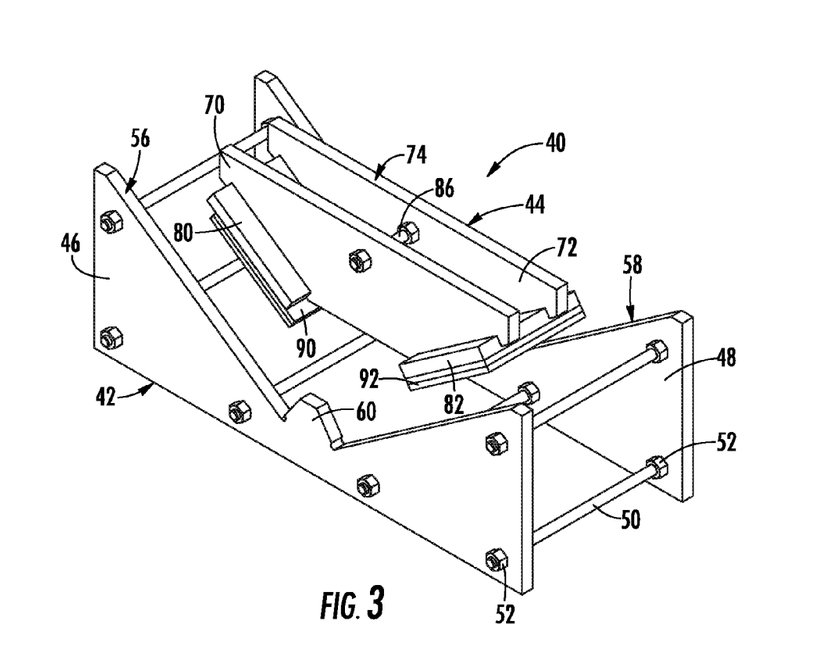
FIG. 3 shows a perspective view of a dynamic test fixture according to one embodiment.

FIGS. 3-6 show an embodiment of a dynamic test fixture 40. The fixture 40 may include a support plate assembly 42, or support, and a load plate assembly 44, or load assembly. The assemblies 42, 44 are not connected to each other in this embodiment, but are shown in their relative positions as they may be situated on a conventional compression testing machine with grates 32, or structures, positioned between them. The support plate assembly 42 may include parallel, spaced support plates 46, 48 that may also be parallel to a central longitudinal plane of the support plate assembly 42. The support plates 46, 48 are secured to each other by support plate spacer rods 50, which may be elongated threaded fasteners such as bolts, of which there are six in this embodiment of a support plate assembly 42. The support plate spacer rods 50 hold the support plates 56, 58 in place with nuts 52 on each side of each support plate 46, 48. The spacing of the support plates 46, 48 is set such that the rails 14 of the grates rest on the left and right sloped surfaces 56, 58 of the support plates 46, 48. The support plates 46, 48 have a top surface that is symmetrically angled on a left sloped surface 56 and a right sloped surface 58 to be shaped substantially like a "V" such that the slopes may be equal in magnitude and have opposite slope. The left and right sloped surfaces 56, 58 may be at an angle θ relative to horizontal (FIG. 3).

At the central lower portion of the top surface, between the left and right sloped surfaces 56, 58, a protrusion that is a center stop 60 may be provided. Each of the left and right sloped surfaces 56, 58 may be configured to receive and support a section of grate (not shown) to be tested. The grates may be placed on the left and right sloped surfaces 56, 58 to abut a center stop 60. The stop 60 may extends upward from the region where the sloped surfaces 56, 58 would intersect absent the stop 60, proximate to where the sloped surfaces terminate at a central portion of the support plate assembly 42, and separates the ends of the grates 32.

Figure 7:
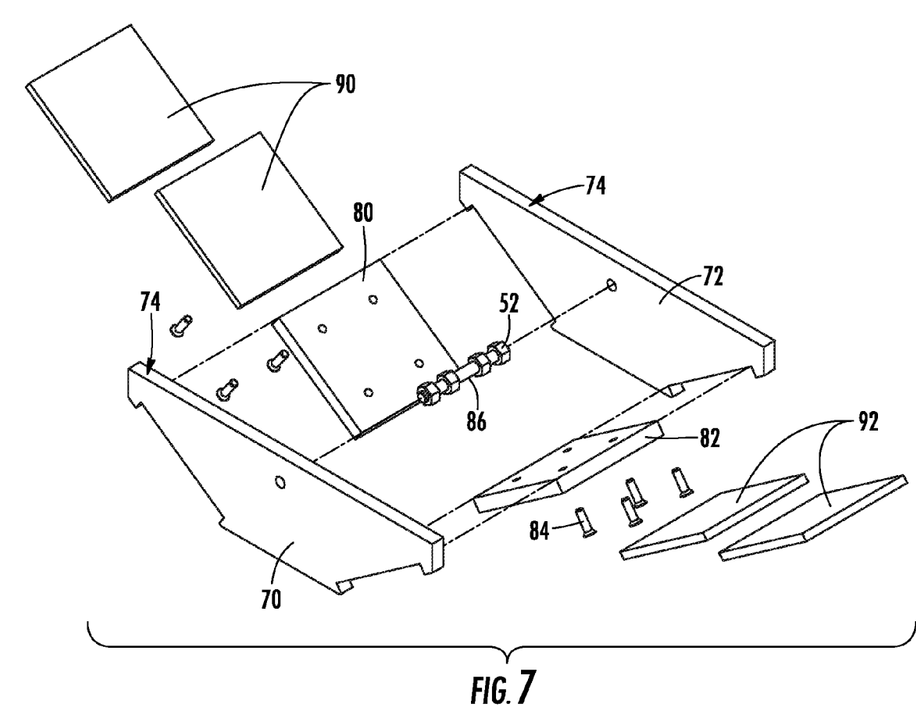
FIG. 7 shows an exploded perspective view of a load plate assembly of the dynamic test fixture of FIG. 3.

Also as shown in FIG. 7, the load plate assembly 44 may include at least one, and in the embodiment shown, two parallel, spaced load plates 70, 72, or load members, that are parallel to a central longitudinal plane of the load plate assembly 44. Each load plate 70, 72 has a top surface 74 and, on angled left and right lower sides, load contact plates 80, 82 or load applying portions that are attached to the load plates 70, 72. In one method attachment the load contact plates 80, 82 are attached to the respective load plates 70, 72 with plate-retaining screws 84, which may be countersunk into the load contact plates 80, 82. The load plates 70, 72 may be held together with a centered load plate clamp rod 86, which may be an elongated threaded rod such as a bolt held in place with nuts 52 on each side of the load plates 70, 72, and the attached load contact plates 80, 82. The load contact plates 80, 82 do not necessarily contact the grates 32, as one or more of buffer plates 90, 92 may be provided on and adjacent to the bottom surfaces of the respective load contact plates 80, 82; in this embodiment two are shown on each load contact plate 80, 82.

Figure 4:
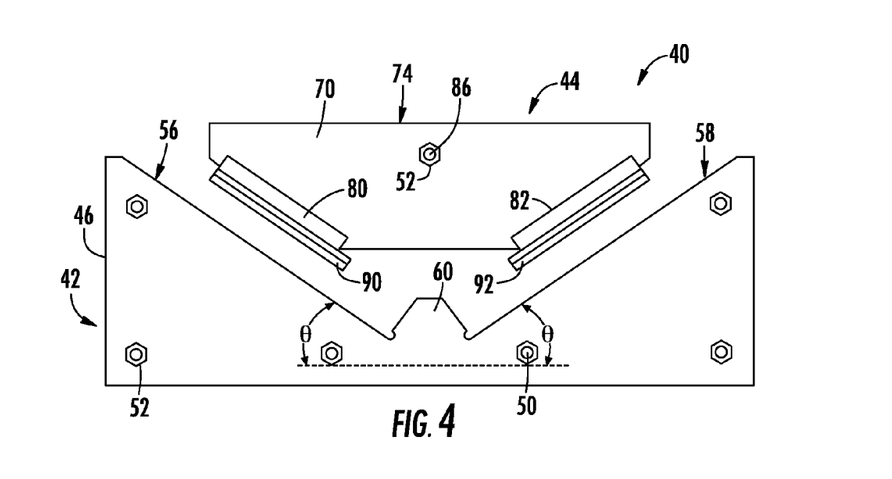
FIG. 4 shows a front elevation view of the dynamic test fixture of FIG. 3; the rear elevation view is identical.
Figure 5:
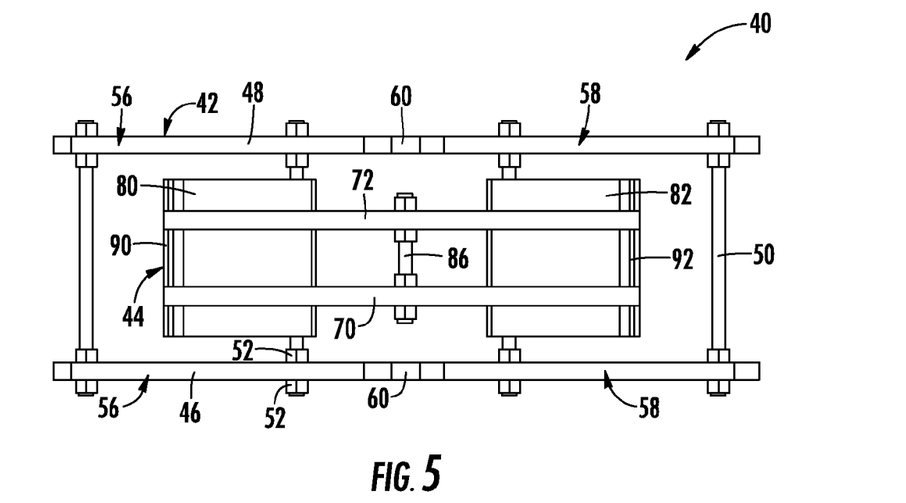
FIG. 5 shows a top plan view of the dynamic test fixture of FIG. 3.
Figure 6:
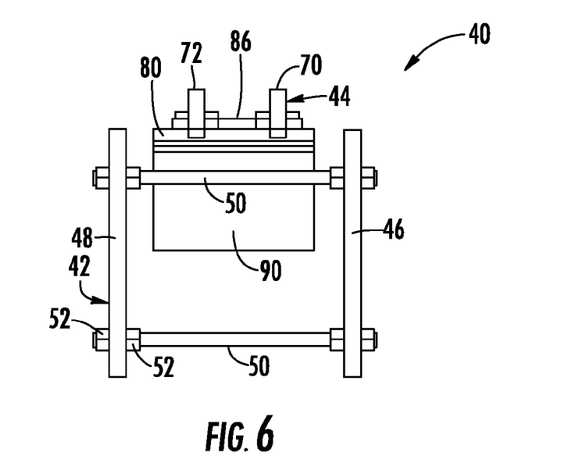
FIG. 6 shows a left end elevation view of the dynamic test fixture of FIG. 3; the right end elevation view is identical.

The bottom surfaces of the load contact plates 80, 82 and accordingly the bottom surfaces of the buffer plates 90, 92, are configured to be parallel to the left and right sloped surfaces 56, 58 of the support plates 46, 48 when the load plate assembly 44 is positioned centered over and in longitudinal alignment with the support plate assembly 42, as shown in FIG. 4, with the respective central longitudinal planes parallel and in vertical alignment. Accordingly, a first surface of the first load contact plate 80 and a second surface of the second load contact plate 82 are at angle θ relative to horizontal. As shown in FIG. 5, the load plate assembly 44 is narrower than the support plate assembly 42, as necessitated by the requirement to apply a load to the grates 32 between the rails 34 as opposed to on the rails 34.

The entire fixture 40, except for the buffer plates 90, 92, may be, for example, fabricated from steel. In one embodiment where the width of a grate 12 is 12 inches or more, the load contact plates 80, 82 may be 9 inch by 9 inch plates. In other embodiments where the width or the grate is 12 inches or less, the load contact plate 80, 82 may be 75% of the trench width wide by 9 inches long. The buffer plates 90, 92 may be, for example, wood, and in one embodiment the buffer plates 90, 92 may be oriented strand board (OSB). OSB may provide distributed loading, which is desirable for simulating the load presented by a vehicle tire; other materials may be as selected by one of ordinary skill in the art. The buffer plates 90, 92 shown are not connected to each other or to the load contact plates 80, 82, but in one embodiment could be held in place with double face tape for convenience. One purpose of the buffer plates may be to avoid high stress point contacts and to better retain a distributed load pattern on the grates, instead of converting into a double line load upon grate deflection during testing.

Figure 8:
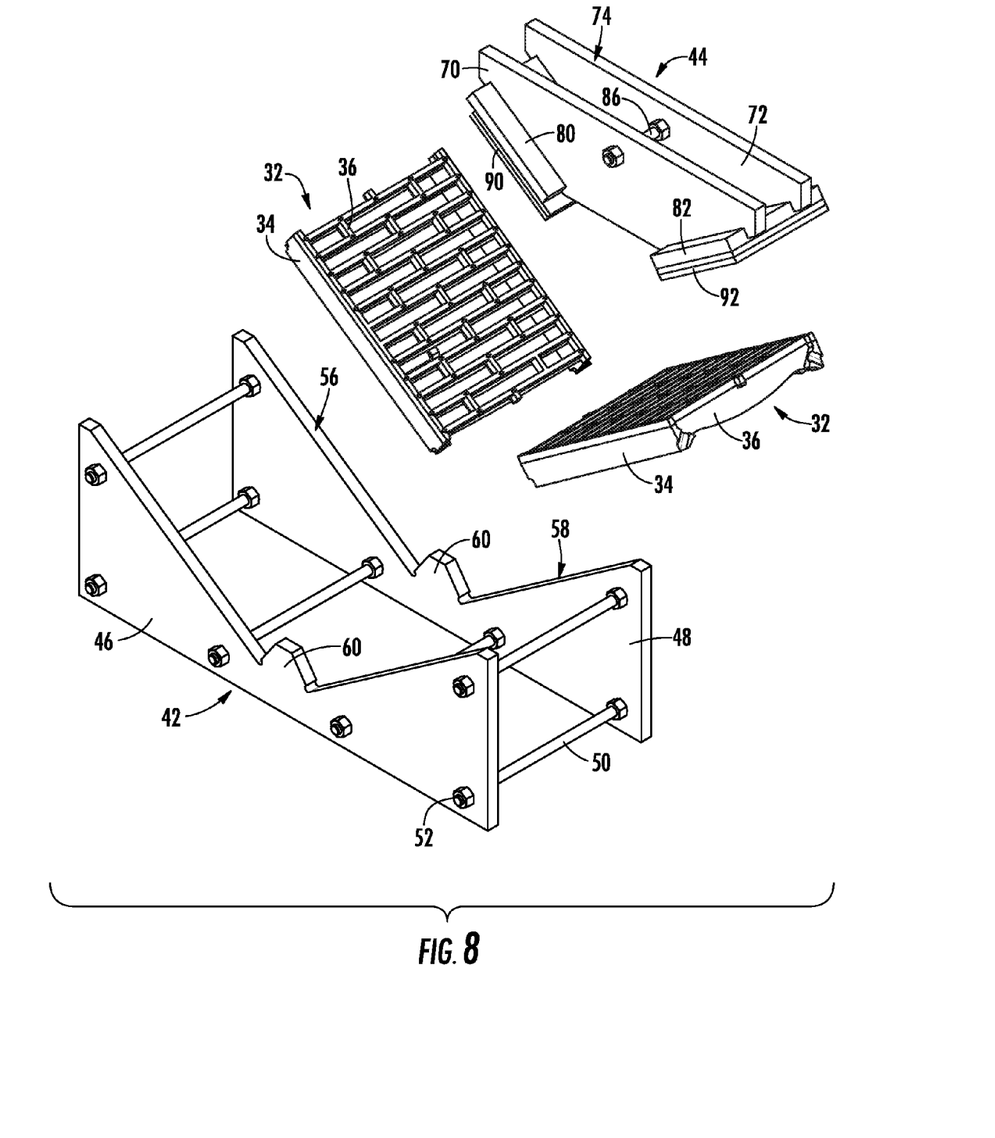
FIG. 8 shows a perspective view of separated load plate assembly and support plate assembly components of the dynamic test fixture of FIG. 3, with trench drain grate test structures.
Figure 9:
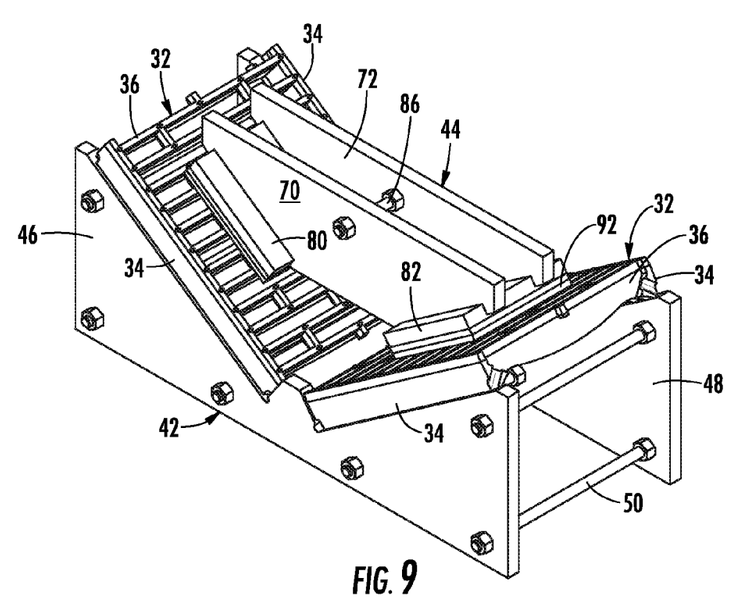
FIG. 9 shows a perspective view of the load plate assembly and the support plate assembly of the dynamic test fixture of FIG. 3, with trench drain grate test structures in place in the fixture.
Figure 10:
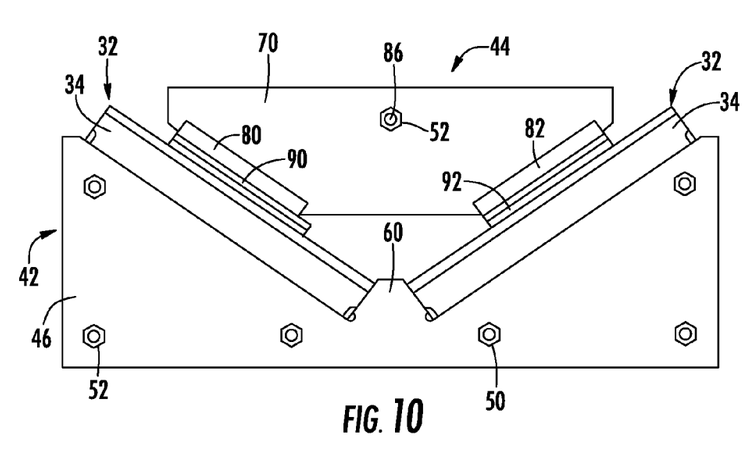
FIG. 10 shows a front elevation view of the dynamic test fixture of FIG. 3 with trench drain grate test structures in place in the fixture.

FIGS. 8-10 show the test fixture 40 with grates 32. Two grates 32, which may be an embodiment of test structures or structures, may be placed on the support plate assembly 42 to allow the fixture 40 to function properly, as in this embodiment there needs to be load applied from both load contact plates 80, 82 and resisted on both the left and right sides of the support plate assembly 42. The rails 14 could be parallel and continuously supported by the sloped surfaces 56, 58, as shown, or in another arrangement could, for example, be positioned transverse to the sloped surfaces 56, 58. In the embodiment shown, horizontal components of the force applied by the load contact plates 80, 82 offset, or substantially offset, each other as the horizontal component of the force applied by one load contact plate 80 is equal to or substantially equal to the horizontal component of the force applied by the other load contact plate 82 and in the opposite direction. Alternatively, one of the two grates 32 could be replaced with a blank, for example, a plate, if only one grate 32 is desired to be tested. The plate would be the same thickness as the grate 32 to provide proper load distribution.

In the embodiment shown, the fixture 40 is configured to accommodate a grate that is 34 inches wide and 0.5 m long. In one embodiment, the support plates 46, 48, the load plates 70, 72, and the load contact plates 80, 82 may be 1 inch thick, and the buffer plates 90, 92 may be 0.875 inches total thickness, but the thicknesses and dimensions may be designed to be compatible with the grate to be tested. The support plate spacer rods 50 and the load plate clamp rod 86 may be, for example, 0.75-inch diameter. The angle θ of the left and right sloped surfaces 56, 58 of the support plates 46, 48 may vary from that shown as needed to approximate the horizontal component of force expected to be experienced at a site of use of the grate 32.

Figure 11:
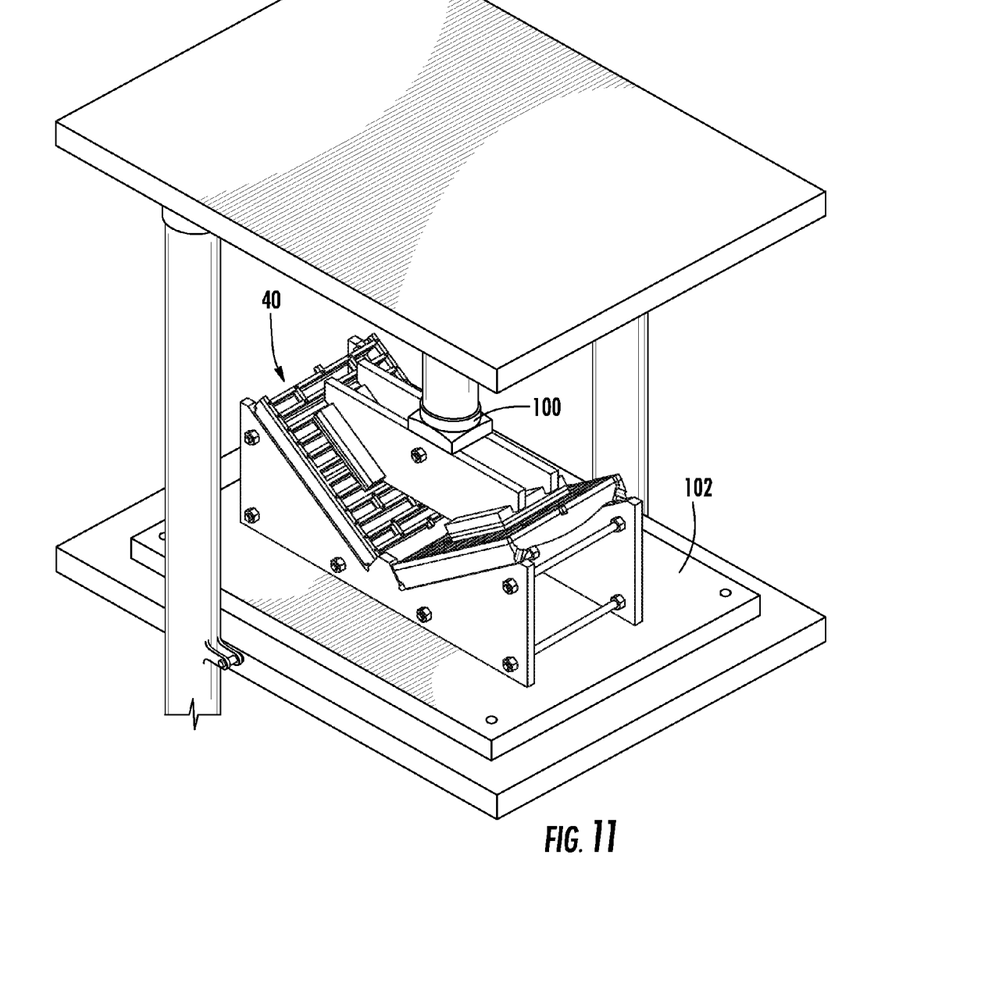
FIG. 11 shows a perspective view of the dynamic test fixture of FIG. 3 positioned in a proof load compression machine.

A test fixture 40 with structures 32 that are grates is shown in FIG. 11 on a compression machine, with the fixture 40 positioned between the upper platen 100 and the lower platen 102. An example of one procedure for use of the fixture 40 and testing of a grate 32 may be as follows. First, the support plate assembly 42 is configured to provide proper support for the grate's side rails 34. Proper support is achieved by setting the spacing of the support plates 46, 48 with the support plate rods 50 to a width that accepts and will continuously support the rails 34. Then the correct width load contact plates 80, 82, as appropriate for the width of grate 32 being tested as described above, are installed in the load plate assembly 44. The support plate assembly 42 may secured in the middle of the test press lower platen using means available with the test press, such as a clamp. Identical grates 32 are then placed on both sides of support plate assembly 42, being the left sloped surface 46 and the right sloped surface 48, and the grates 32 are slid longitudinally until the end of the grates 32 rest against the center stop 60. The offsetting horizontal components of force on the grates 32 helps to maintain only a vertical force on the compression machine, which generally is not designed to withstand lateral forces.

A test fixture 40 with grate test structures 32 is shown in FIG. 11. The load plate assembly 44 is positioned such that it contacts both grates 32 centrally and equally. The load plate assembly 44 should not be secured to the test press upper platen 100 so that the load plate assembly 44 is free to equalize under a load. A load is then applied to the grates 32 until reaching a specified failure mode using, for example, the same test parameters as used in AASHTO M306 procedures. The application of the load may be at a specified acceleration, which in the embodiment shown is 0.7 g. In some embodiments, the specified failure mode may be first failure. The test may be stopped at the first failure minimize lateral test loads on the test press. First failure may be, for example, breakage of a cross-bar 16 of the grate 32. However, if the load plate assembly 44 has a relatively high freedom of movement or the test presses are built to better resist lateral loads, the first failure criterion would not be an important or limiting factor with respect to testing to additional failure modes.

It is understood that instead of being oriented with an upper platen 100 being oriented above a lower platen 102, the compression machine and test fixture 40 could be oriented at any angle, for example, with the force being applied through the platens horizontally rather than vertically and the test fixture 40 likewise rotated 90 degrees.

Force Vector Math may be used to determine how the test load is divided into the vertical load and the horizontal load on the grate. The actual longitudinal load at failure may be calculated using trigonometric functions and based upon the fixture configuration and the applied press load. The longitudinal load is the component of the load along the direction parallel to the rails of the grate. For example, if the angle θ is 35 degrees, and the load at first failure is 100,000 lbs., then the longitudinal load at failure is calculated as 100,000 lbs.×tan 35°=70,000 lbs.

Although specific embodiments have been illustrated and described herein, those of ordinary skill in the art appreciate that any arrangement which is calculated to achieve the same purpose may be substituted for the specific embodiments shown and that the embodiments herein have other applications in other environments. For example, the fixture 40 is shown and described above as configured for applying a longitudinal load component (in the direction parallel to the rails 34 of the grates 32 along with a vertical component. However, by rotating the grate and the load and support members 90 degrees, the concept is also applicable to testing of combined transverse and vertical loads as well. Instead of the sloped surfaces 56, 58 substantially forming a "V" shape, they could be inverted to substantially from an upside-down "V", which would also provide offsetting horizontal components of force. Components could be attached to each other by means other than threaded fasteners, such as by welding. This application is intended to cover any adaptations or variations of the present disclosure. The following claims are in no way intended to limit the scope of the disclosure to the specific embodiments described herein.

What is claimed is:

1. A test fixture apparatus for testing first and second structures with a compression testing machine, the apparatus comprising:

a support plate assembly including two spaced, parallel support plates in fixed relation and parallel to a first central longitudinal plane, the support plate assembly having sloped surfaces associated with each support plate to support the first structure at a first angle relative to horizontal and the second structure at a second angle relative to horizontal, the first angle and the second angle being of equal magnitude and opposite slope; and a load plate assembly configured to oppose the support plate assembly, the load plate assembly including at least one load plate parallel to a second central longitudinal plane and configured to allow the load plate assembly to apply a load to the first structure and to the second structure in response to application of force to the support plate assembly, load plate assembly, or a combination thereof in a direction other than perpendicular to the sloped surfaces.

2. The test fixture apparatus of claim 1, further comprising a first load contact plate having a first surface and a second load contact plate having a second surface, the first load contact plate and the second load contact plate each mounted to the at least one load plate, wherein when the load plate assembly opposes the support plate assembly with the first and second structures disposed therebetween and the first and second central longitudinal planes are parallel and in vertical alignment, the first surface of the first load contact plate is oriented at the first angle relative to horizontal and the second surface of the second load contact plate is a oriented at the second angle relative to horizontal.

3. The test fixture apparatus of claim 2, wherein the first load contact plate and the second load contact plate each have a width that is transverse to the second central longitudinal plane and that is less than the distance between the support plates.

4. The test fixture apparatus of claim 2, further comprising at least one buffer plate adjacent to the first surface of the first load contact plate and at least one other buffer plate adjacent to the second surface of the second load contact plate.

5. The test fixture apparatus of claim 1, wherein the support plates are spaced by a distance transverse to the first central longitudinal plane that permits rails of the first structure to be received by the sloped surfaces that are at the first angle and rails of the second structure to be received by the sloped surfaces that are at the second angle.

6. The test fixture apparatus of claim 5, wherein the rails of the first structure and the rails of the second structure are parallel to the support plates.

7. The test fixture apparatus of claim 1, wherein the sloped surface at the first angle and the sloped surface at the second angle associated with each support plate terminate proximate to each other with a stop disposed therebetween.

8. The test fixture apparatus of claim 7, wherein the stop comprises a protrusion configured to separate the first structure and the second structure.

9. The test fixture apparatus of claim 1, wherein the sloped surface at the first angle and sloped surface at the second angle associated with each support plate slope downward from each respective outer end of the support plate toward a central portion of the support plate to terminate proximate to each other.

10. The test fixture apparatus of claim 1, wherein the sloped surfaces at the first angle and sloped surfaces at the second angle on each support plate slope upward from each respective outer end of the support plate toward a central portion of the support plate to terminate proximate to each other.

11. The test fixture apparatus of claim 1, wherein when the load plate assembly opposes the support plate assembly with the first central longitudinal plane parallel and in vertical alignment with the second central longitudinal plane, and with the first structure and the second structure disposed therebetween, a vertical force applied results in substantially equal and opposite horizontal components of force on the first structure and the second structure.

12. The test fixture apparatus of claim 1, wherein the at least one load plate comprises two spaced, parallel support plates in fixed relation.

13. A test fixture apparatus for testing first and second structures with a compression testing machine, the apparatus comprising:
a support having sloped surfaces configured to support the first structure at a first angle relative to horizontal and the second structure at a second angle relative to horizontal, the first angle and the second angle being of equal magnitude and opposite slope; and
a load assembly configured to oppose the support, the load assembly including:
at least one load member configured to allow the load assembly to apply a load to the first structure and to the second structure in response to application of force to the support, load assembly, or a combination thereof in a direction other than perpendicular to the sloped surfaces; and
a first load applying portion having a first surface and a second load applying portion having a second surface.

14. The test fixture apparatus of claim 13, wherein when the load assembly opposes the support with the first and second structures disposed therebetween, the first surface of the first load applying portion is oriented at the first angle relative to horizontal and the second surface of the second load applying portion is oriented at the second angle relative to horizontal, and a force applied in a direction that substantially bisects the angle formed by the sloped surfaces results in substantially equal and opposite horizontal components of force on the first structure and the second structure.

15. The test fixture apparatus of claim 14, wherein each sloped surface at the first angle terminates proximate to a corresponding sloped surface at the second angle with a stop disposed therebetween.

16. The test fixture apparatus of claim 15, wherein the stop comprises a protrusion configured to separate the first structure and the second structure.

17. The test fixture apparatus of claim 14, wherein the sloped surfaces are spaced by a distance that are configured to permit rails of the first structure to be received by the sloped surfaces that are at the first angle and rails of the second structure to be received by the sloped surfaces that are at the second angle, wherein the rails of the first structure and the rails of the second structure are parallel to each other.

18. A method of testing first and second structures using a test fixture, comprising:
placing the first structure on a support that supports the structure at a first angle relative to horizontal;
placing the second structure on the support, the support supporting the second structure at a second angle relative to horizontal of equal magnitude and opposite slope to the first angle; and
applying a load to the first structure in a first direction and to the second structure in a second direction until reaching a failure mode of at least one structure.

19. The method of claim 18, wherein applying the load to the first structure in a first direction comprises applying a load through a first plate having a surface parallel to the first angle and applying the load to the second structure in a second direction comprises applying a load through a second plate having a surface parallel to the second angle.

20. The method of claim 18, wherein the first structure and the second structure are grates each having a top and a bottom, each grate comprising parallel rails and cross-bars extending therebetween, and further comprising applying force in a second direction to the bottom of the rails with the support and applying force in an opposite third direction to the cross-bars.

21. The method of claim 18, wherein placing the first structure on a support and placing the second structure on the support comprises placing the first structure and the second structure on a support plate assembly including two spaced, parallel support plates in fixed relation and parallel to a first central longitudinal plane, the support plate assembly having sloped surfaces associated with each support plate to support the first structure at a first angle relative to horizontal and the second structure at a second angle relative to horizontal, the first angle and the second angle being of equal magnitude and opposite slope; and
wherein applying a load to the first structure in a first direction and to the second structure in a second direction comprises applying a load to a load plate assembly having a second central longitudinal plane and configured to oppose the support plate assembly, the load plate assembly including at least one load plate parallel to the second central longitudinal plane and configured to allow the load plate assembly to apply a load to the first structure and to the second structure in response to application of force to the support plate assembly, load plate assembly, or a combination thereof in a direction other than perpendicular to the sloped surfaces.

22. A method of making a test fixture for testing first and second structures, comprising:

assembling two support plates to be spaced, parallel, and in fixed relation, each support plate having sloped surfaces to support the first structure at a first angle relative to horizontal and the second structure at a second angle relative to horizontal, the first angle and the second angle being of equal magnitude and opposite slope; and assembling two load plates to be spaced, parallel, and in fixed relation;

mounting a load contact plate to each load plate, the load contact plates configured to apply a load to the first structure and to the second structure in response to application of force to the support plates, load plates, or a combination thereof in a direction other than perpendicular to the sloped surfaces.

23. The method of making a test fixture of claim 22, wherein assembling the support plates comprises attaching the support plates to each other with elongated threaded fasteners and nuts.

24. The method of making a test fixture of claim 23, wherein assembling the load plates comprises attaching the load plates to each other with elongated threaded fasteners and nuts.

25. The method of making a test fixture of claim 24, wherein mounting load contact plates to the load plates comprises attaching the load contact plates to the load plates with threaded fasteners.

26. The method of making a test fixture of claim 25, further comprising varying the spacing of the support plates and the load plates with use of varying length threaded fasteners and varying width load contact plates to accommodate varying width structures.

* * * * *